United States Patent [19]

Makower et al.

[11] Patent Number: 5,474,057
[45] Date of Patent: Dec. 12, 1995

[54] LAPAROSCOPIC DISSECTION TENSION RETRACTOR DEVICE AND METHOD

[75] Inventors: Joshua Makower, Nanuet; Lois Fitton, New York, both of N.Y.; Aaron Sodickson, Waban; Bill Gorman, Essex, both of Mass.

[73] Assignee: Valleylab Inc., Boulder, Colo.

[21] Appl. No.: 278,976

[22] Filed: Jul. 21, 1994

Related U.S. Application Data

[63] Continuation of Ser. No. 20,494, Feb. 22, 1993, abandoned.

[51] Int. Cl.⁶ .................................................. A61B 17/00
[52] U.S. Cl. .................. 600/214; 606/205; 606/206; 600/218; 600/205; 600/226
[58] Field of Search .................................................. 128/20

[56] References Cited

U.S. PATENT DOCUMENTS

| | | | |
|---|---|---|---|
| 3,035,582 | 5/1962 | Seiger | 606/205 |
| 4,054,143 | 10/1977 | Bauer. | |
| 4,378,810 | 4/1983 | Ishizaki et al. | 128/754 |
| 4,646,751 | 3/1987 | Maslanka. | |
| 4,763,668 | 8/1988 | Macek et al.. | |
| 4,763,669 | 8/1988 | Jaeger. | |
| 4,872,456 | 10/1989 | Hasson. | |
| 4,880,015 | 11/1989 | Nierman. | |
| 5,059,198 | 10/1991 | Gimpelson | 606/207 X |
| 5,147,373 | 9/1992 | Ferzli. | |
| 5,152,780 | 10/1992 | Honkanen et al.. | |
| 5,176,699 | 1/1993 | Markham | 606/206 |
| 5,195,505 | 3/1993 | Josefsen. | |
| 5,195,506 | 3/1993 | Hulfish. | |
| 5,195,507 | 3/1993 | Bilweis. | |
| 5,201,759 | 4/1993 | Ferzli. | |
| 5,209,747 | 5/1993 | Knoepfler. | |
| 5,263,967 | 11/1993 | Lyons, III et al. | 606/205 |
| 5,281,220 | 1/1994 | Blake, III | 606/205 X |
| 5,282,826 | 2/1994 | Quadri | 606/207 |
| 5,312,391 | 5/1994 | Wilk | 606/1 |
| 5,318,013 | 6/1994 | Wilk | 128/20 |

FOREIGN PATENT DOCUMENTS

| | | | |
|---|---|---|---|
| 1342650 | 7/1987 | U.S.S.R. | 606/157 |
| 1597177 | 10/1990 | U.S.S.R. | 128/751 |
| WO92/14412 | 9/1992 | WIPO. | |
| WO92/19146 | 11/1992 | WIPO. | |
| WO92/20292 | 11/1993 | WIPO. | |

*Primary Examiner*—Richard J. Apley
*Assistant Examiner*—Beverly M. Flanagan
*Attorney, Agent, or Firm*—Peter C. Richardson; Lawrence C. Akers; Aaron Passman

[57] ABSTRACT

A minimally invasive retractor and dissector for internal surgical use on a patient's body has a tubular support for passing into the patient's body. A proximal end on the tubular support located outside the patient's body is in position to provide access for the surgeon. A distal end on the tubular support located inside the patient's body to provide access within the patient for surgery. A control is located at the proximal end of the tubular support. One or more articulated members are movably positioned relative to the distal end of the tubular support so each of the articulated members allows swinging relative to the distal end. A rotator connects to the proximal end of the tubular support for movement relative to the control. An instrument moves independently of the tubular support when the articulated members and the distal tips cooperatively function on the tissue. The instrument passes simultaneously through a passage from the proximal end to beyond the distal end so the articulated members may position the tissue relative to the patient.

23 Claims, 6 Drawing Sheets

5,474,057

LAPAROSCOPIC DISSECTION TENSION RETRACTOR DEVICE AND METHOD

This application is a continuation of application Ser. No. 08/020,494 filed on Feb. 22, 1993, now abandoned.

FIELD OF THE INVENTION

This relates to minimally invasive instruments for operating through an opening into a patient's body on tissue therein and more particularly, the ability to stretch and surgically alter the tissue with a minimally invasive dissector and retractor passing through the opening.

BACKGROUND OF THE DISCLOSURE

Frequently, during minimally invasive procedures several trocars are placed through the patient's body for access into a cavity therein. One trocar could provide illumination and video, another insufflation and another minimally invasive operative instruments.

Surgery through a trocar inserted opening through for example, the tissue of the patient's abdominal wall has become an important means to minimize the extent of surgical invasion. The lessening of invasion improves the cosmetic result, shortens recovery and lowers the cost. Minimally invasive internal surgical procedures and equipment are available and in use for a variety of medical operations including gall bladder, bowel and gynecological surgery. A proper and simple instrument to retract and dissect through the opening is needed.

Tension on tissue is the fundamental tenet of all surgical technique. When the dissection field is held under tension, tissue being cut readily spreads away from the cutting tool. This allows for the safe and rapid identification of underlying structures, and provides a clear dissection path through which the surgeon can focus in on the deeper target.

In the minimally invasive setting, with as few as three instrument carrying openings or portals into the abdomen, the ability to cut tissue under tension is currently not feasible. The two instruments in use are often taken up holding larger structures (i.e., the gallbladder, or bowel) out of the way. This compels the surgeon to bite and tear away the overlying friable fascia using forceps, leaving clumps of tissue and debris at the sides of the microsurgical site. Often, underlying structures are inadvertently cut or misidentified due to the inability of the surgeon to create tension at the site.

If the surgeon had a reliable way of placing tension on the tissue at the wound, without giving up other instrumentation or creating another transabdominal puncture, this could reduce significantly the number of bile duct and vascular injury complications, and increase the ease with which the procedure is accomplished. Bile duct injuries occur at a rate of 0.2 to 3%, are a serious complication when present, and sometimes require open surgical revision.

Currently, disposable minimally invasive graspers and dissectors for laparoscopy account for millions in sales, with strong growth expected.

There is a wide variety of generic scissors and grasping forceps, as well as some slightly more specialized tools intended for grasping specific organs such as the gall bladder or bowel. Less invasive or minimally invasive surgical procedures are growing in frequency of use and complexity. Such procedures include: laparoscopy, thoracoscopy, endoscopy, etc.

SUMMARY OF THE INVENTION

The dissector and retractor may have one or more grasping or tissue holding tips at the end of one or more articulated members and a passage through which another instrument may be passed. The members are designed such that they may be moved away from the axis of their tubular support so that tension may be created on internal tissue. The passage is designed to allow other instruments (i.e., cutters, graspers, scissors, or energized devices-laser, electrocautery, scopes, staples and clip appliers, etc.) to be passed therethrough so they may be directed towards the tissue under tension. The members may be separately designed to swing apart, lock together or slide longitudinally with respect to each other, and may be used interchangeably. The retractor and dissector provides for direct tissue tension and support by the surgeon while cutting (and that is not always possible with current instrumentation), the tension members are carried on the tubular support and the instrument for operating may use the passage therein, reducing the number of openings necessary for operation. Use of the dissector and retractor may stabilize the cutting implement with respect to the tissue under tension in a way not possible with current instrumentation. The tubular support acts as a safety extension of the opening allowing instruments to be exchanged quickly without the need to move an observation scope during entry. The distal end of the tubular support is located such that rapid exchange of the instruments through the tubular support is facilitated. The dissector and retractor is compatible with the technique of not using gas to insufflate the abdomen and may be used around the scope. It can dissect a path for the scope, and subsequently stabilize its position in difficult to reach areas, or areas that are moving.

The minimally invasive retractor and dissector for internal surgical use on a patient may have a tubular support for passing into the body. A proximal end on the tubular support is preferably located outside the patient's body in position to be accessed by the surgeon and may include a gas lock in the nature of a hemostasis valve. A distal end on the tubular support is preferably located inside the patient's body in position to provide access for the surgeon. A means movably carried on the tubular support may have one or more jointed articulated members movably positionable and capable of holding and pulling tissue disposed beyond the distal end.

The tubular support includes a passage through which access may be gained substantially along an axis thereof during operative procedures on the internal tissue of the patient. An instrument capable of moving independent of the means for cooperative functioning on the tissue most preferably simultaneously passes through the passage from the proximal end to beyond the distal end so the means may position the tissue relative to the patient and the instrument. The instrument is preferably a surgical tool and the tissue is maneuvered by the means within the body into a position relative to the surgical tool. The surgical tool may be an electrosurgical device.

The means include at least one member extending beyond the distal end and movable relative thereto; the member for holding and pulling tissue within the patient when the instrument is movable relative to tissue held by the member. The means may alternately include a pair of arms disposed beyond the distal end and movable relative thereto, the pair of members hold tissue therebetween and the surgical instrument is movable relative to tissue held between the pair of members. Each member has a distal tip configured to hold tissue. Each tip may include at least a hook located thereon for access to the tissue or each tip may include a pair of graspers mounted thereon for gripping or spreading tissue thereadjacent or each tip may include a pair of scissors mounted thereon for gripping, spreading or cutting tissue thereadjacent.

The members may be forceps extending beyond the distal end; the forceps can be operative for opening, closing and holding the tissue. One or more of the members might include a suction tube for holding and maneuvering tissue beyond the distal end and within the patient.

A control at the proximal end may preferably be provided to manipulate the means; the control permits holding and pulling tissue disposed beyond the distal end relative to the axis. The control is capable of moving the instrument independent of the means for operating on the held and maneuvered tissue within the body beyond the distal end. The means may be articulated by the control for movement within the body relative to the axis. The instrument may also be articulated by the control for movement within the body relative to the axis. The control may have a grip for manipulating the means and a handle for operating the instrument.

The tubular support is on one embodiment a pair of U-shaped channels that cooperate to form an elongate tube composed of conjugating parts movable in the direction of the axis relative to one another.

A method for using a minimally invasive retractor and dissector for internal surgery on a patient may have steps. A step may be making an opening for a tubular support for passing into the body followed by the step of leaving a proximal end on the tubular support located outside the patient's body in position to be accessed by the surgeon. Then the next step may be positioning a distal end on the tubular support inside the patient's body in position to provide access for the surgeon. Another step is moving a means carried on the tubular support and having one or more jointed articulated members positioned and capable of holding and pulling tissue disposed beyond the distal end.

The additional steps may preferably be holding and pulling tissue disposed beyond the distal end of the tubular support. The added step of using a passage through the tubular support for access substantially along an axis thereof during operative procedures on the internal tissue of the patient may also be followed. A further added step of moving an instrument in the passage and independent of the means for cooperative functioning on the tissue simultaneously may be desirable.

DETAILED DESCRIPTION OF THE INVENTION

Figure 1:
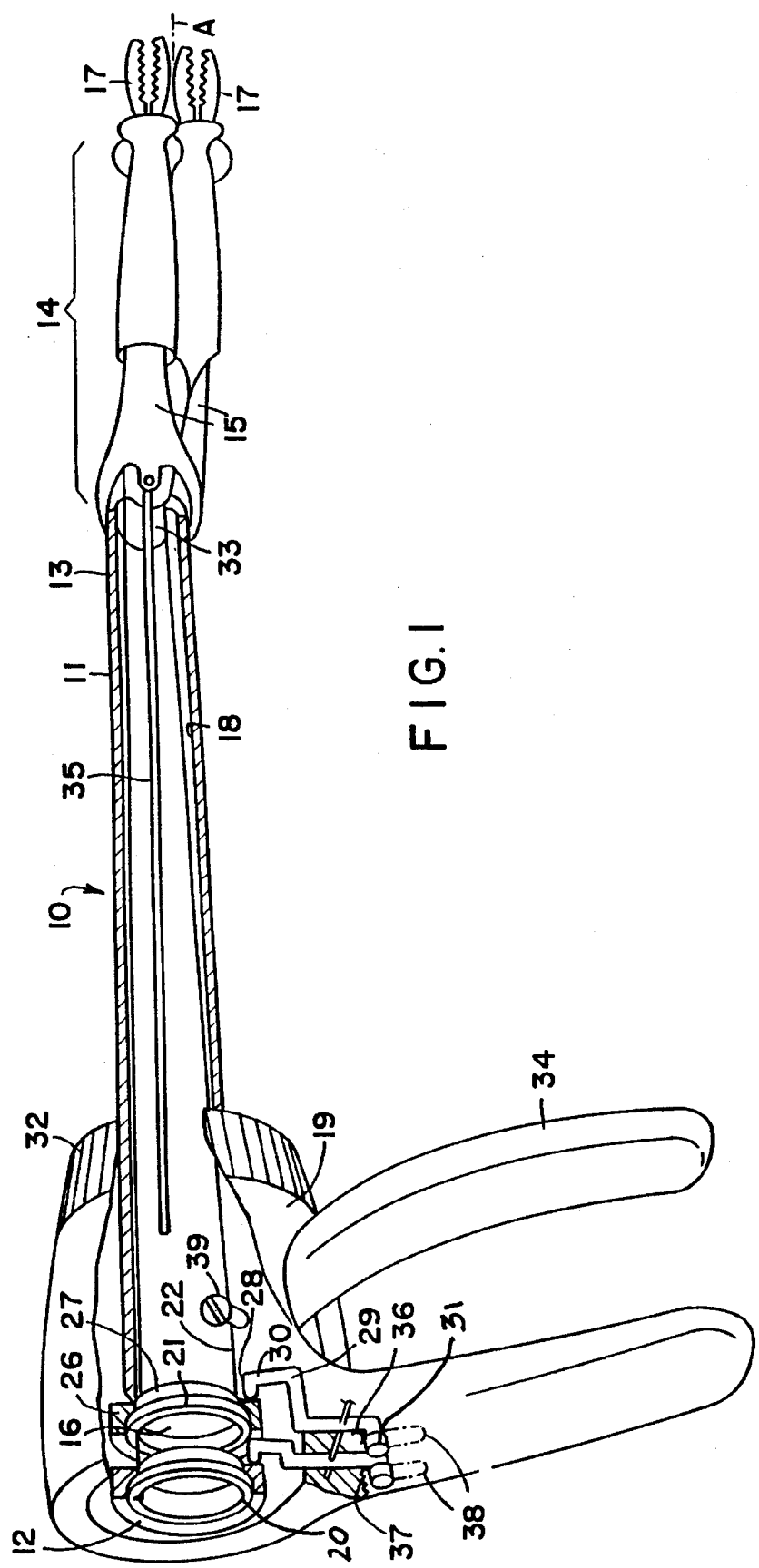
FIG. 1 is a perspective view of the minimally invasive retractor dissector of the present invention shown partially cut away to depict the operation of the members by the control.

FIG. 1 shows a partially cut away perspective view of a minimally invasive retractor and dissector 10 for internal surgical use on a patient. There is a tubular support 11 for passing into the body such as through a trocar opening or a cannula placed in the body. In a particular example for laparoscopic use a trocar or cannula placed through the abdominal wall into an insufflated body cavity would be an appropriate place for the tubular support 11. The tubular support 11 has a proximal end 12 located outside the patient's body and positioned to be accessed by the surgeon; a gas lock in the form of a hemostasis valve can be used. A distal end 13 on the tubular support 11 is positioned inside the body to provide access to the organs within the insufflated cavity. Means 14 are movably carried on the tubular support 11 near the distal end 13 thereof. Specifically, one or more jointed articulated members 15 are movably positioned and capable of holding and pulling tissue disposed beyond the distal end 13. The tubular support 11 in FIG. 1 includes a passage 16 in the form of a lumen through which access may be gained substantially along an axis "A" thereof during an operative procedure on the internal tissue of the patient. The passage 16 permits free axial access to the area between the articulated members 15 for use as an extra way for an additional instrument to enter the body through the passage 16 of the tubular support 11.

The additional instrument capable of moving independently of the means 14 provides a cooperative functioning ability to handle the tissue simultaneously. In particular, the instrument passes through the passage 16 from the proximal end 12 to beyond the distal end 13 so that while the means 14 position the tissue relative to the patient and the instrument, the instrument can be independently moved and operated. In one approach, the instrument is a surgical tool and the tissue is maneuvered by the means 14 within the body into position relative to the surgical tool. A particular surgical tool could be, for example: a scalpel, an electrosurgical device, such as a coagulator or cutter, or merely video camera or a telescope. See FIG. 2 for an example of the cooperation of the tool or instrument and the means 14.

Figure 5A:
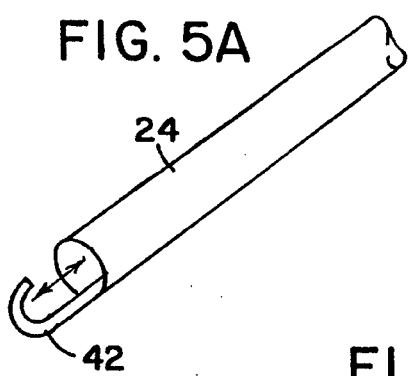
FIG. 5 A through F illustrates in perspective various tip configurations that may be used with each member as alternates.
Figure 5B:
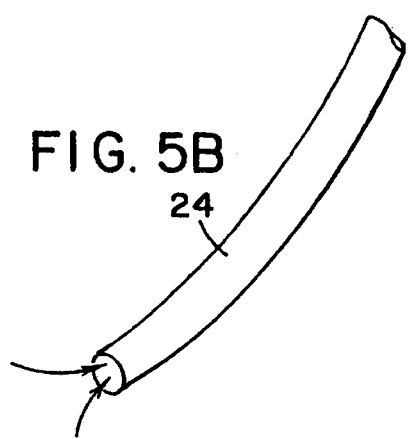
Figure 5F:
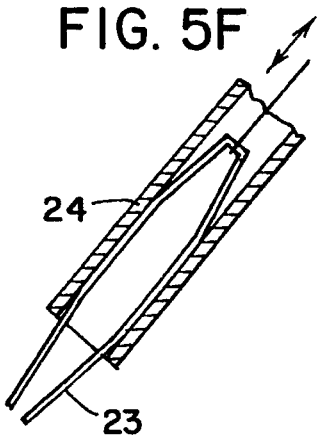
Figure 5C:
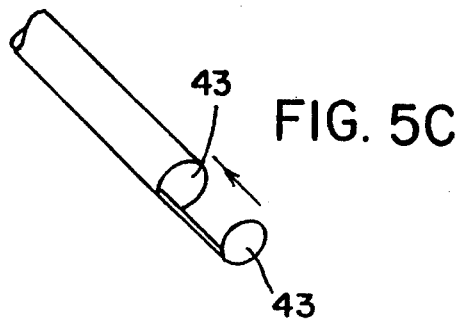
Figure 5D:
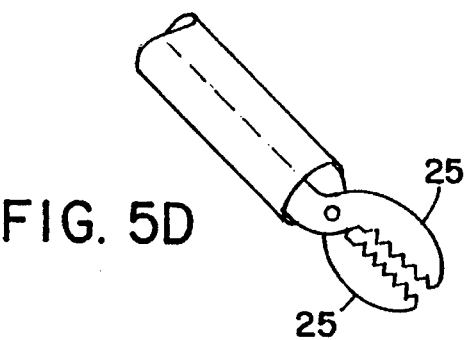
Figure 5E:
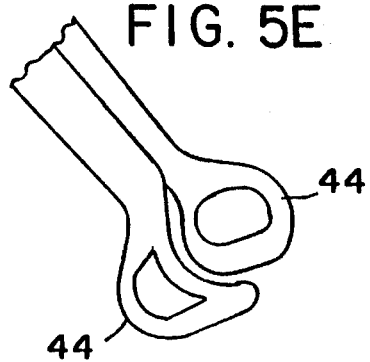
Figure 6:
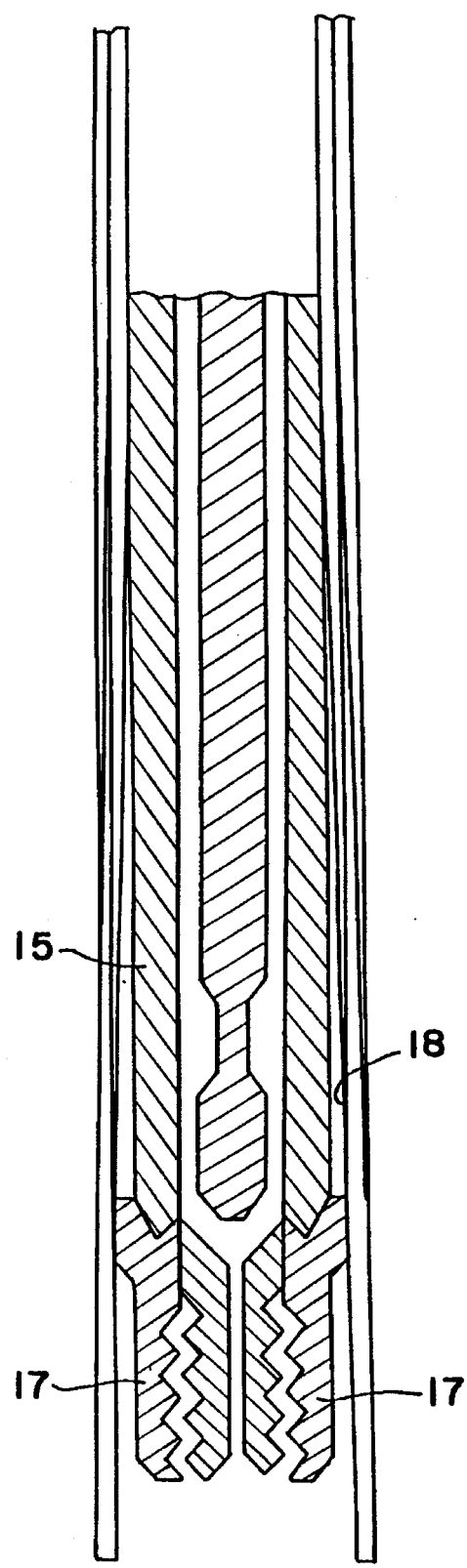
FIG. 6 is a side view in cross section showing a way in which the minimally invasive retractor dissector may collapse to fit through the tubular support.

The means 14 include at least one member 15; in the various FIGS. 1, 2, 3, and 6, two members 15 are shown but that is not required. If the passage 16 needs to be larger than it is with two members 15, one member 15 is sufficient, however in circumstances where the maximum flexibility is required, two members 15 may be used with varying tips 17, as will be explained in connection with FIGS. 5A through F. The members 15 extend beyond the distal end and are movable relative thereto. In some of the views, such as FIG. 1, 2, 3 and 6, the members 15 are pivotally mounted on the distal end 13 of the tubular support 11 and it is also possible that the members 15 could be carried for further axial movement relative to the distal end 13 instead of pivoting or swinging relative thereto since that might be a simple mechanism wherein the member 15 slides relative to and along an inside wall 18 of the tubular support 11. FIG. 6 suggests such an approach. The tip 17 of the member 15 is moveable relative to its member such that when it is positioned within the cavity and relative to the axis "A" of the tubular support 11, tissue may be held. Consequently, the maneuvering of internal organs or tissue is easily accomplished by means of having the member 15 carried on the tubular support 11 movable relative thereto.

In FIG. 1, there is a control 19 at the proximal end 12 of the tubular support 11. The control 19 manipulates the means 14 and the tips 17. The control 19 permits holding and pulling tissue disposed beyond the distal end 13 in directions relative to the axis "A" of the tubular support 11. The control 19 permits moving the instrument within the passage 16 independent of the means 14 for operating on the held and maneuvered tissue within the body beyond the distal end 13 thereof.

Members 15 are preferably in the form of a pair of arms disposed beyond the distal end 13 and carried for movement relative to the distal end 13 for maximum flexibility in use. Such an arrangement could tend to restrict the window provided by the passage 16 through the tubular support 11. Shown in the partially cut away portion of FIG. 1 is one form of the control 19 for the members 15 wherein a pair of conjugating inner rings 21 carried about and with the proximal end 12 of the tubular support 11 are used to operate the tips 17 of the members 15. These inner rings 21 are allowed to freely rotate relative to their respective outer rings 26 but not one another thus allowing the surgeon to rotate the control 19 relative to the tip 17 during placement which will make the minimally invasive retractor dissector 10 easy to use. An inner ring 21 is connected by a depending cable 22 to the tip 17 so that axial movement of the cable 22 will close the normally open tip 17 in the preferred embodiment into a clamping position. In particular, if the tip 17 is a forceps 23 as in FIG. 5F in a tube 24, then axial movement of cable 22 in the axial direction of the arrows and toward the practitioner will draw the forceps 23 into the tube 24 and thus together to pinch tissue therebetween. The cable 22 extends along the inside wall 18 of the tubular support 11 from beyond the distal end 13 to the proximal end 12. The cable 22 is guided along the members 15 to the tip 17 to connect to the normally open graspers 25 in FIG. 5D or forceps 23 in FIG. 5F thereat for control thereof. The connection of cable 22 with forceps 23 is shown in the embodiments in FIGS. 2 and 5F wherein the transfer of axial motion is applied differently.

To operate the cable 22 there is an outer ring 26 circumscribing a depending wall 27 on the inner ring 21 and conjugating with an inward turned flange 28 on which the inner ring 21 sits and within which the depending wall 27 conjugates. Lifting the outer ring 26 will in turn raise the inner ring 21 and axially move the cable 22 attached to the inside thereof. The outer and inner rings 26 and 21 allow free rotary motion therebetween while control of the closure of the tips 17 remains unaffected by rotation. Specifically, to raise the outer ring 26 a bell crank 29 pivotally mounted to the control 19 is used. The bell crank 29 has an inward point 30 that engages the outer ring 26 and button actuators 31 located through the control 19 for easy access by the surgeon. Pushing on the button actuators 31 will lift the cables 22 and the conjugate inner rings 21 while still allowing rotation of the control 19 relative to the tubular support 11. Another set of rings 20 are used when there are two sets of tips 17 to be operated. The second set of rings 20 can function the same as the first and are positioned axially above the first in FIG. 1. A serrated band 32 about the base of the control 19 may be used to rotate tubular support 11 to position tips 17 to enhance use and easing hand position relative to the location of the tips 17. The outer rings 26 rotate with the tubular support 11.

Figure 2:
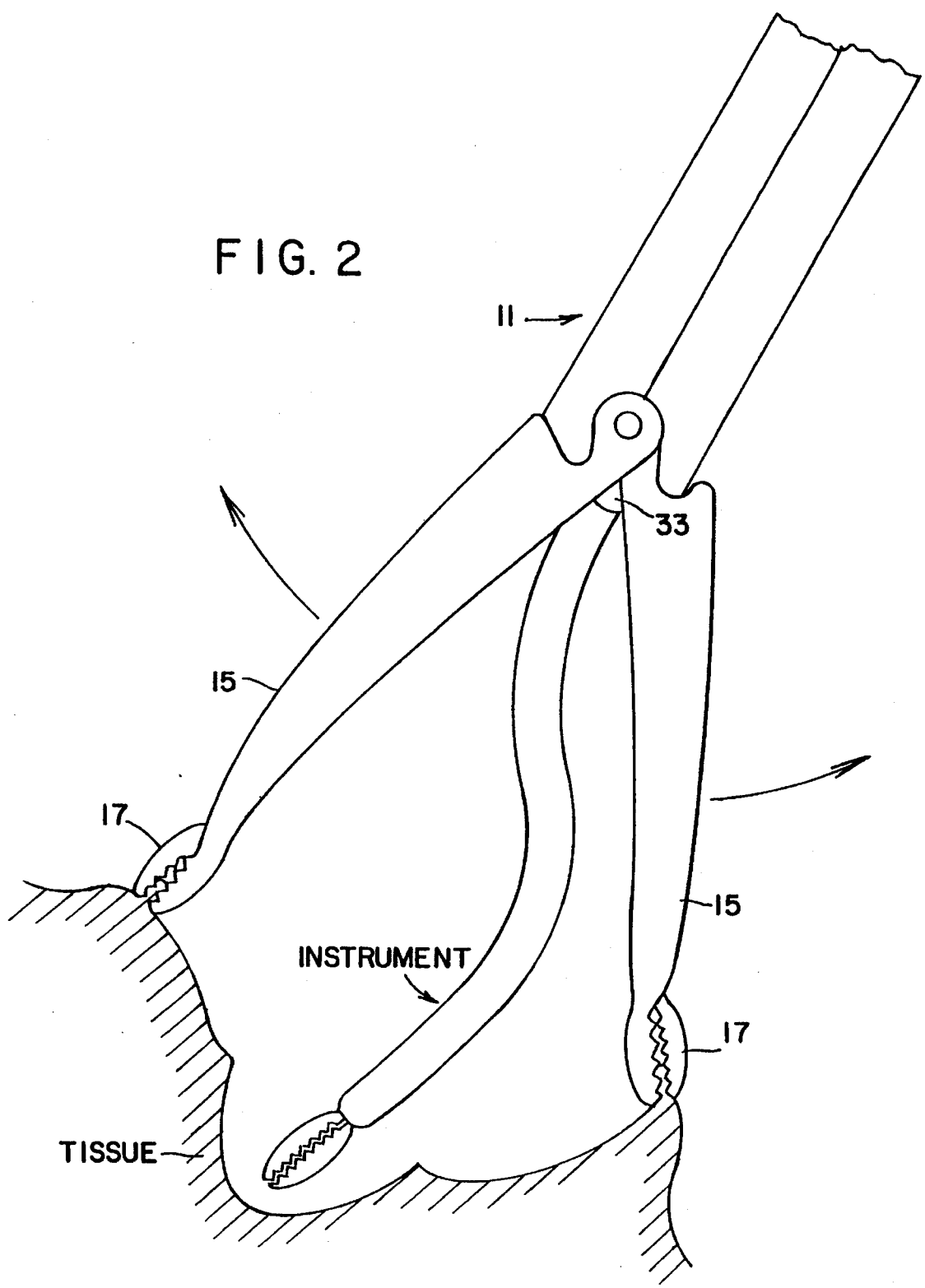
FIG. 2 is an enlarged partial perspective view of the members and an instrument therebetween wherein the tissue when held taut can be operated on by the instrument.
Figure 7:
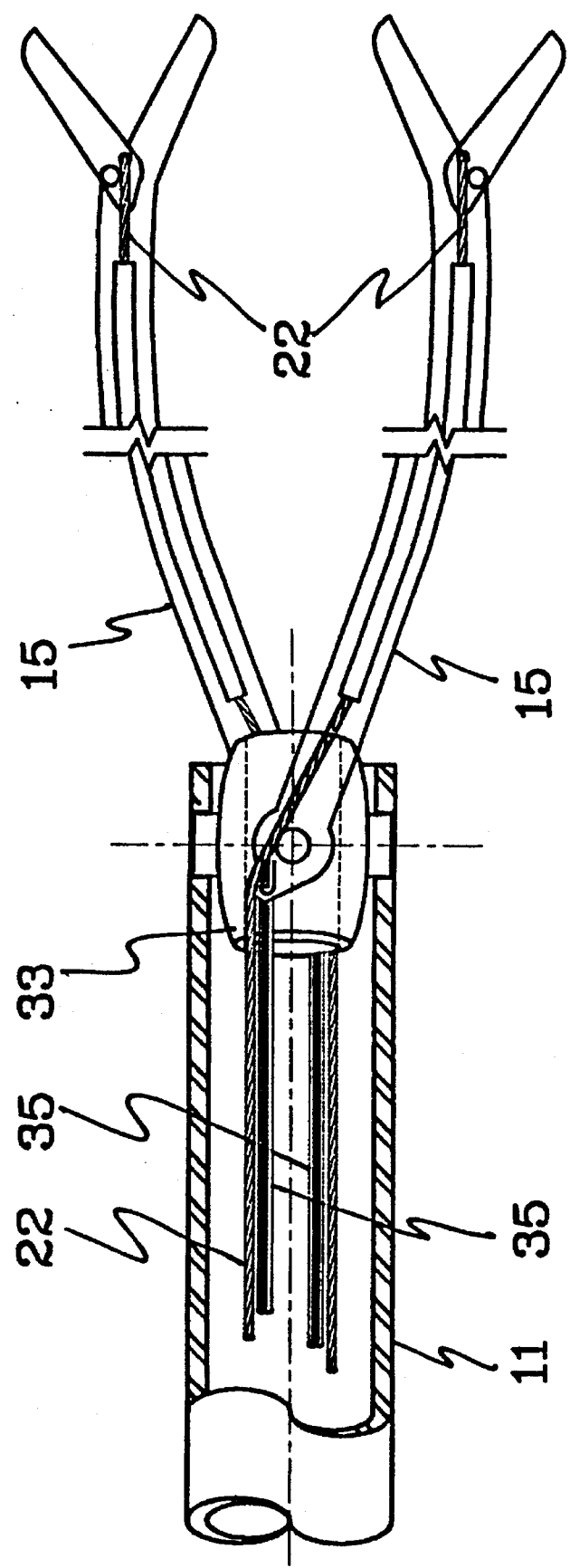
FIG. 7 is a side view in partial cross section of the tubular support distal end depicting the directional olive and the articulated members movably mounted thereto with tips supported thereon.

A directional olive 33 is located at the distal end 13 of the tubular support 11 so that the members 15 mounted thereto are able to swing relative thereto in more than one plane. The directional olive 33 is like a yoke for a universal joint except that it is hollow along the direction of the axis of the tubular support 11. There are crossed lines for pivoting in a plane normal to the axis of the tubular support 11 so the hollow center of the directional olive 33 can be swung about the crossed lines of pivot from side to side or up and down relative to the distal end 13 of the tubular support 11. In particular, the normal position of the members 15 are juxtaposed as shown in FIG. 1 and the members 15 are spring loaded to rest in that position. When it is desired to separate the members 15, then one tip 17 is clamped onto some tissue as will be explained herein and as shown in FIG. 2 so that at least one of the members 15 is applied. After that the tubular support 11 can be maneuvered to separate the members 15 so that the free member 15 is pointed to another area of tissue and then clamped thereto. Tension can then be applied to the tissue spanning between the tips 17 by way of a spreader grip 34 on the control 19. While only one rod 35 is identified in the figures, two are preferred; FIG. 7 shows two rods 35. Specifically, the spreader grip 34 in FIG. 1 is connected to rods 35 that pass along the inside wall from the spreader grip 34 to the members 15 near the directional olive 33. Axial movement of the rods 35 when the surgeon squeezes the spreader grip 34 pulls on the members 15 to spread them apart at their tips 17 as shown in FIGS. 1 and 2. Though not specifically shown, the connection between spreader grip 34 and rods 35 allows rotary motion of rods 35 relative to the spreader grip 34 and is similar to inner and outer rings for the cables 22. The connection between rods 35 and grip 34 is centrally open. Remembering that the normal position of the members 15 is together the force of the rods 35 acts to separate then against the spring load. The directional olive 33 allows the members 15 to pivot while maintaining the passage 16 open; that is, the olive 33 is as explained hollow or centrally unimpeded and while able to pivot relative to the distal end 13 does not interfere with the passage 16. The spring loading of the members 15 can be integral with the members 15 so that they each are made from an elastic material which is bent to load them into a normally closed position with enough force. Similarly, the graspers 25 at the tips 17 could be spring loaded to be normally closed and can be pulled open by the cables 22 although that is not the preferred approach; the approach preferred is to be normally open as shown in FIG. 2.

Shown in the cut away in FIG. 1 is a latch 36 for each of the actuator buttons 31. There is a tooth edge 37 on the housing that can engage one or more steps on each actuator buttons 31. To release the engagement, each actuator button 31 is pulled back against a spring 38 to separate the step from the tooth edge 37. A similar lock 39 is provided for the spreader grip 34 so that the members 15 can be held in position, i.e. spread apart.

Figure 3:
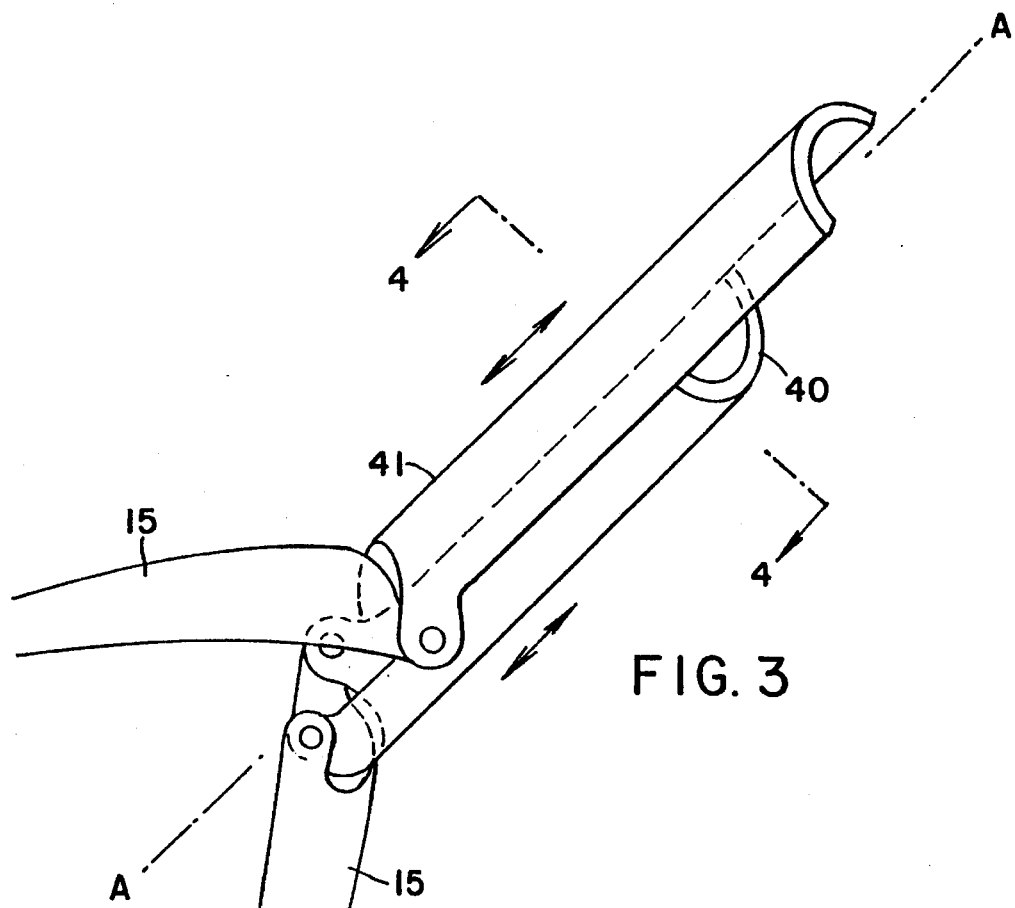
FIG. 3 is a partial perspective view of a particular tubular support having cooperative U-shaped conjugating channels that are able to slide axially relative to one another.
Figure 4:
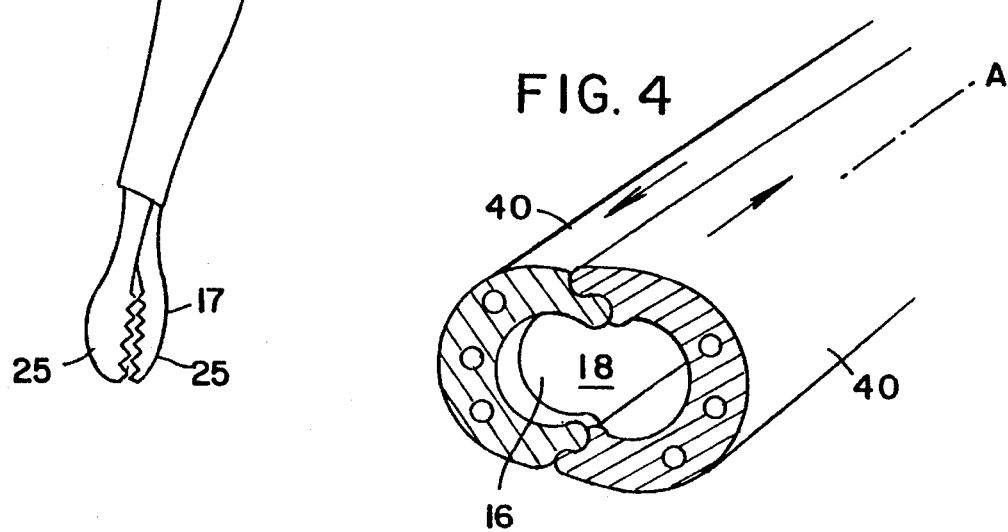
FIG. 4 is an enlarged cross sectional view taken along line 4—4 of FIG. 3 and showing the conjugation of the U-shaped channels.

In FIGS. 3 and 4, an alternate embodiment of the tubular support is shown as a pair of U-shaped channels 40 that cooperate and form an elongate tube 41 composed of conjugating parts movable in the direction of the axis "A" relative to one another. FIG. 4 specifically shows one way in which the conjugating parts are associated with one another. It is clear that the relative movement of the U-shaped channels 40 provides an additional degree of flexibility for the members 15 relative to one another so that they may be not only be swung apart from one another, but also moved axially relative to one another. The end cross sectional view of FIG. 4 is enlarged to show the detail of conjugation.

The tubular support 11 can be made out of any material appropriate for the nature of its use and in particular a medical grade plastics, metals or ceramics may be used, however, the choice of material will undoubtedly be determined by the function of the particular configuration. While elongate tube 41 can be easily extruded U-shaped channels 40, machining in addition to extrusion, or molding may be needed to obtain the desired cross-sectional configuration necessary. It is expected that skilled artisans will be able to fashion a tubular support 11 from single or multiple pieces in a way which provides a thin wall and allows a maximum passage 16 therethrough while providing adequate strength for carrying the members 15 at the distal end 13 thereof.

FIG. 5 illustrates a variety of tips 17; each tip 17 disclosed may be used to hold and/or move tissue or organs within the body. These various tips 17 are located at the end of the members 15 in position for placement within the body. Specifically, FIG. 5A has a retracting hook 42 which can be slid axially in the direction of the arrows to pinch or hold the tissue therewithin. A tube 24 and cooperating hook 42 are shown for that purpose and the double arrow therein illustrates the directions of axial movement of the hook 42 relative to the tube 24, although it is preferred that the hook 42 be normally open and merely pulled closed.

FIG. 5B shows a suction tube which can also be used to hold the tissue. Vacuum applied to the suction tube 24 can be intermittently activated in order to catch tissue and hold it. The suction tube 24 should be a semi rigid material to afford maximum control. FIG. 5C shows a pair of plates 43 in the nature of a vise which can be axially moved relative to one another in order to clamp tissue therebetween. FIG. 5D shows a pair of graspers 25 in the nature of the jaws of a pliers which may be used to clamp tissue. The graspers 25 are normally apart and are pulled together to hold tissue.

FIG. 5E has a pair of tongs 44 which may be used to hold the tissue instead of gripping it with the teeth of the graspers 25 shown in FIG. 5D. The various configurations shown are not limiting. Other arrangements may be used as desired for specific needs in connection with the members 15 and medical procedures. In particular, scissors, see FIG. 7, can be mounted instead of the graspers 25 shown in FIG. 5D. Forceps 23 can be mounted so that they are a pair of bent together leaf springs which are held within the tube 24 as in FIG. 5F; the cable 22 pulls them into the tube 24 or pushes them axially out of the tube 24 or when released from the pull of cable 22 spring apart as the forceps 23 move axially outward of the tube 24 as desired. The bend of the forceps 23 being contained within the tube 24 is attached to the member 15, which is movable relative to the distal end 13 of the tubular support 11.

In FIG. 6 is shown a schematic rendering of how each member 15 could contain a tip 17 arrangement. The tubular support 11 encases a pair of members 15 held therein and when the members 15 are moved axially into and out of the tubular support 11, they may spread apart or move together laterally, respectively.

Specifically, an instrument within the passage 16 may be moved axially relative to the tubular support 11 into and out of the body cavity while the means 14 are moved, for example, by swinging or rotating away from the axis "A" such that the maximum use may be obtained from the entry portal occupied by the tubular support 11 through the patient's body wall. As described, the means 14 may be articulated by rods 35 connected to the spreader grip 34 and bell cranks 29 to the actuator buttons 31 operate the tips 17 so that the members 15 spread within the body while tissue is held. It is also possible that the rods 35 could be used to slide a pair of distally supported members 15 axially into and out of the tubular support 11 and move them relative to the instrument which can be handled individually and manually as it passes from the proximal end 12 to the distal end 13 through the passage 16. Therefore, while all motion might be axial, it can be independent.

A method for using the minimally invasive retractor and dissector 10 for internal surgery on a patient includes various steps. Making an opening for the tubular support 11 for passing into the body through, for example, an abdominal wall in a laparoscopic procedure for removal of gall bladder or a uterus or the like is ordinarily accomplished by a trocar with a flesh cutting end which passes through the body and leaves an opening of about 10 mm in diameter. After the opening has been prepared, the tubular support 11 can be inserted into the opening and positioned within the body so that its distal end 13 is in the cavity and the members 15 associated therewith are in position for handling tissue therewithin. Another step in the method is leaving the proximal end 12 of the tubular support 11 located outside the patient's body and positioned to be accessed by the surgeon such that control of the means 14 within the body is easily accomplished. The surgeon may then position the distal end 13 on the tubular support 11 relative to the patient's body and allow access for the surgeon by way of the means 14 therein to handle the tissue or organs during a procedure. It is the means 14 which are moved by the surgeon through the control 19 so that tissue in the body can be held or pulled as desired even though it is disposed beyond the distal end 13 of the tubular support 11. The tubular support 11 can, to some degree, be moved in and out of the body or relative to the abdominal wall for example such that the distal end 13 is positioned near the tissue or organ of interest, so that the means 14 within the body are able to be used most effectively. The passage 16 through the tubular support 11 can then be used for access substantially along its axis "A" during the operative procedure on the internal tissue of the patient and in particular a video, surgical device or other instrument may be passed through the passage 16 into the body cavity. The instrument may thereby may be able to cooperatively function on the tissue simultaneously but independently of the means 14. The instrument is inserted into a placed trocar while the distal end 13 thereof is viewed with a camera or scope in another portal during the entry of the instrument. The surgeon can rotate the tubular support 11 by its control 19 so that satisfactory hand position is achieved. The minimally invasive retractor dissector 10 may then be advanced toward the tissue to be retracted and/or dissected. A member 15 with a tip 17 having a forceps 23 or grasper 25 is clamped on a piece of tissue located slightly lateral with respect to the desired plane of dissection. The opposite member 15 is positioned by means of the control 19 over toward the other side of the dissection plane and the tip 17 thereon is applied to the tissue thereat. After the tips 17 are in position holding the tissue the members 15 are spread apart by the surgeon with pressure on the grip 34 that controls the member 15 positions. Tension on the dissection site is thereby obtained and can be gradually applied as desired and needed by the surgeon.

A second surgical instrument may then be inserted through the passage 16 or any other port for dissection of the tissue under tension. As the tissue is dissected by the surgeon additional tension may be applied to pull or spread the fascia away from the site. As required or desired one or both of the graspers 25 or forceps 23 at the tips 17 of each member 15 can be repositioned to clamp tissue at a different place for further dissection after suitable tension retraction. If required the surgeon can at any time release the clamping or tension as easily as the placement was attained. If the passage 16 is used for the surgical instrument, then movement of the tubular support 11 will act to guide the surgical instrument. An olive 33 located near the distal end 13 of the tubular support 11 acts to guide the instrument inserted therethrough during movement of the tubular support 11 relative to the tensioning members 15.

What is claimed is:

1. A minimally invasive retractor and dissector for internal surgical use on a patient's body comprising:

a tubular support for passing into the patient's body including a passage through which access may be gained substantially along an axis "A" thereof during operative procedures on the internal tissue of the patient;

a proximal end on the tubular support located outside the patient's body in position to provide access into the patient for the surgeon;

a distal end on the tubular support located inside the patient's body in position to provide access within the patient for surgery;

a plurality of articulated members movably positioned relative to the distal end of the tubular support and one of the articulated members for allowing swinging thereof relative to the distal end;

a distal tip on the articulated members, each distal tip configured to move independently of each other distal tip and hold tissue so any one of the articulated members is capable of holding and pulling tissue disposed beyond the distal end of the tubular support;

a control located at the proximal end of the tubular support, and a rotator connected to the proximal end of the tubular support and operatively connected to the articulated members for rotatably positioning the tubular support and the articulated members within the patient's body for movement relative to the control.

2. The minimally invasive retractor and dissector of claim 1 wherein the articulated members as the distal tip includes forceps extending beyond the distal end, the forceps operative for opening, closing and holding the tissue.

3. The minimally invasive retractor and dissector of claim 1 wherein at least one of the articulated members include as the distal tip a suction tube for holding and maneuvering tissue beyond the distal end and within the patient independently of the other of the members.

4. The minimally invasive retractor and dissector of claim 1 wherein the control manipulates each of the plurality of articulated members, said control thereby permitting the tips to independently hold and pull tissue disposed beyond the distal end of the tubular support.

5. The minimally invasive retractor and dissector of claim 1 wherein the at least one of the articulated members is articulated by the control for independent movement within the patient's body relative to the axis "A".

6. The minimally invasive retractor and dissector of claim 1 wherein the tubular support is a pair of U-shaped channels that cooperate to form an elongate tube composed of associated parts independently movable along the axis "A" and relative to one another.

7. A minimally invasive retractor and dissector and an instrument for internal surgical use by a surgeon on a patient's body comprising:

a tubular support for passing into the patient's body including a passage through which access may be gained substantially along an axis "A" thereof during operative procedures on the internal tissue of the patient;

a proximal end on the tubular support located outside the patient's body in position to provide access into the patient for the surgeon;

a distal end on the tubular support located inside the patient's body in position to provide access within the patient for surgery;

a control located at the proximal end of the tubular support permitting holding and pulling tissue disposed beyond the distal end relative to the axis "A";

at least one articulated member movably positioned relative to the distal end of the tubular support and one of the articulated members for allowing swinging thereof relative to the distal end in more than one plane;

a distal tip on the articulated members, each distal tip configured to move independently of each other distal tip and hold tissue so the articulated members are capable of holding and pulling tissue disposed beyond the distal end of the tubular support;

a rotator connected to the proximal end of the tubular support and operatively connected to the articulated members for rotatably positioning the tubular support and the articulated members within the patient's body for movement relative to the control, and an instrument capable of moving independent of the tubular support, the articulated members, and the distal tips, for cooperatively functioning on the tissue, the instrument passing through the passage from the proximal end to beyond the distal end so the articulated members may position the tissue relative to the patient.

8. The minimally invasive retractor and dissector of claim 7 wherein the passage is unimpeded to receive the instrument capable of moving independently of the articulated members and movably carried to cooperatively function on the tissue, the instrument arranged to simultaneously pass through the passage from the proximal end to beyond the distal end so the articulated members may hold and position the tissue relative to the patient's body and the instrument, the instrument may thereby operate on the tissue held by the articulated members.

9. The minimally invasive retractor and dissector of claim 8 wherein the articulated members carry at least one tip being articulatable and extending beyond the member is movable relative thereto the tip for holding tissue within the patient's body while the instrument is movable relative to tissue held by the tip.

10. The minimally invasive retractor and dissector of claim 10 wherein the surgical tool is an electrosurgical device.

11. The minimally invasive retractor and dissector of claim 10 wherein the surgical tool is an electrosurgical device.

12. The minimally invasive retractor and dissector of claim 7 wherein the articulated members disposed beyond the distal end are movable independently of one another and hold tissue therebetween and the instrument is movable relative to tissue held between the articulated members.

13. The minimally invasive retractor and dissector of claim 12 wherein each tip includes at least a hook located thereon for access to the tissue.

14. The minimally invasive retractor and dissector of claim 12 wherein each tip includes a pair of graspers mounted thereon for independently gripping or spreading tissue thereadjacent.

15. The minimally invasive retractor and dissector of claim 12 wherein each tip includes a pair of scissors mounted thereon for independently gripping, spreading or cutting tissue thereadjacent.

16. The minimally invasive retractor and dissector of claim 7 wherein the control is connected to the tubular support for moving the tubular support and thereby affecting the instrument passing through the passage independently of the articulated members for operating on the held and maneuvered tissue within the patient's body beyond the distal end.

17. The minimally invasive retractor and dissector of claim 16 wherein the control has a grip for independently manipulating the articulated members and the instrument is separate from the grip for independently maneuvering the instrument relative to the tubular support.

18. The minimally invasive retractor and dissector of claim 7 wherein a directional olive is carried at the distal end of the tubular support and articulated by the control for movement within the patient's body relative to the axis "A" and wherein the instrument within the passage is affected by the movement of the tubular support for movement within the patient's body relative to the axis "A".

19. The minimally invasive retractor and dissector of claim 18 wherein the control has a grip for independently manipulating the articulated members and wherein the instrument can be independently maneuvered by the surgeon with movement of and through the tubular support and wherein the directional olive is moved with the tubular support and with the articulated members.

20. A method for using a minimally invasive retractor and dissector for internal surgery by a surgeon on a patient's body includes the following steps:

providing a tubular support having a longitudinal passage therethrough;

providing the tubular support including a longitudinal passage therethrough, a proximal end, a distal end, a rotator on the proximal end for rotary movement of the distal end, a plurality of independently moveable articulated members at the distal end, each articulated member having a tip thereon capable of holding and pulling tissue within the patient's body;

making an opening for the tubular support for passing into the patient's body;

leaving a proximal end on the tubular support located outside the patient's body in position to be accessed by a surgeon;

positioning a distal end on the tubular support inside the patient's body in position to provide access for the surgeon to the inside of the patient's body;

providing a rotator on the proximal end of the tubular support for rotary movement of the distal end;

moving articulated members positioned on the distal end for movement independently of one another and each articulated member having a tip thereon capable of holding and pulling tissue disposed beyond the distal end, and swinging of one of the articulated members.

21. The method of using the minimally invasive retractor and dissector of claim 20 further comprising holding, pulling and rotating tissue disposed beyond the distal end of the tubular support with the tip on each articulated member.

22. The method of using the minimally invasive retractor and dissector of claim 20 further comprising using the passage through the tubular support for access of an instrument during operative procedures on the internal tissue of the patient.

23. The method of using the minimally invasive retractor and dissector of claim 20 further comprising moving an instrument in the passage and independent of the articulated members for cooperative functioning on the tissue simultaneously.

* * * * *